(12) United States Patent
Hao et al.

(10) Patent No.: US 10,628,412 B2
(45) Date of Patent: Apr. 21, 2020

(54) ITERATIVE VISUALIZATION OF A COHORT FOR WEIGHTED HIGH-DIMENSIONAL CATEGORICAL DATA

(71) Applicant: Hewlett-Packard Development Company, L.P., Houston, TX (US)

(72) Inventors: Ming C. Hao, Palo Alto, CA (US); Michael Hund, Constance (DE); Wei-Nchih Lee, Palo Alto, CA (US); Nelson L. Chang, San Jose, CA (US); Daniel Keim, Constance (DE); Kevin Smathers, Hayward, CA (US); Jishang Wei, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 267 days.

(21) Appl. No.: 15/545,895

(22) PCT Filed: Feb. 20, 2015

(86) PCT No.: PCT/US2015/016893
§ 371 (c)(1),
(2) Date: Jul. 24, 2017

(87) PCT Pub. No.: WO2016/133543
PCT Pub. Date: Aug. 25, 2016

(65) Prior Publication Data
US 2018/0004803 A1    Jan. 4, 2018

(51) Int. Cl.
*G06F 16/00* (2019.01)
*G06F 16/242* (2019.01)
(Continued)

(52) U.S. Cl.
CPC ........ *G06F 16/2428* (2019.01); *G06F 16/248* (2019.01); *G06F 16/2425* (2019.01);
(Continued)

(58) Field of Classification Search
CPC .. G06F 16/951; G06F 16/215; G06F 16/2246; G06F 16/24; G06F 16/245;
(Continued)

(56) References Cited

U.S. PATENT DOCUMENTS 6,263,334 B1    7/2001  Fayyad et al.
6,314,453 B1   11/2001  Hao et al.
(Continued)

OTHER PUBLICATIONS

Chang, Remco, et al.; Scalable and Interactive Visual Analysis of Financial Wire Transactions for Fraud Detection; http://www.cs.tufts.edu/~remco/publications/2008/IVS-wirevis.pdf >, 10 pages.
(Continued)

*Primary Examiner* — Truong V Vo
(74) *Attorney, Agent, or Firm* — Michael A. Dryja

(57) ABSTRACT

Visualization of a cohort for high-dimensional categorical data is disclosed. One example is a system including a display module to identify real-time selection of a query data element in an interactive visual representation of high-dimensional categorical data elements comprising a plurality of categorical components. A matrix generator generates a binary distance matrix with columns representing categorical components, and entries in a row indicative of a degree of similarity of respective categorical components of the selected query data element to a data element represented by the row, and determines a category weighting matrix by associating a weight with entries in each column of the binary distance matrix. An evaluator evaluates a weighted similarity score for a data element represented by a row of the category weighting matrix based on entries of the row. A selector iteratively and interactively selects, based on weighted similarity scores, a cohort of categorical data elements.

15 Claims, 16 Drawing Sheets

(51) Int. Cl.

| | | |
|---|---|---|
| *G06F 16/248* | (2019.01) | |
| *G06F 16/2457* | (2019.01) | |
| *G06F 19/00* | (2018.01) | |
| *G06Q 30/02* | (2012.01) | |

(52) U.S. Cl.
CPC ...... *G06F 16/24578* (2019.01); *G06F 19/326* (2013.01); *G06Q 30/0201* (2013.01)

(58) Field of Classification Search
CPC ............ G06F 16/2455; G06F 16/9535; G06F 3/0484; G06F 16/3347; G06F 16/3334; G06F 16/35
See application file for complete search history.

(56) References Cited

U.S. PATENT DOCUMENTS

| | | |
|---|---|---|
| 6,330,685 B1 | 12/2001 | Hao et al. |
| 6,906,709 B1 | 6/2005 | Larkin et al. |
| 7,343,362 B1 | 3/2008 | Flippen |
| 7,593,013 B2 | 9/2009 | Agutter et al. |
| 8,006,224 B2 | 8/2011 | Bateman et al. |
| 8,392,418 B2 | 3/2013 | Birdwell et al. |
| 2004/0088577 A1 | 5/2004 | Render |
| 2004/0175700 A1 | 9/2004 | Geesaman |
| 2005/0004823 A1 | 1/2005 | Hnatio |
| 2005/0065951 A1 | 3/2005 | Liston et al. |
| 2010/0153389 A1 | 6/2010 | Angell et al. |
| 2012/0131484 A1 | 5/2012 | Neumann et al. |
| 2013/0144676 A1 | 6/2013 | O'Sullivan et al. |
| 2013/0339514 A1 | 12/2013 | Crank et al. |
| 2014/0108379 A1 | 4/2014 | Gotz et al. |
| 2016/0063112 A1* | 3/2016 | Bottum ............... G06F 16/9535 707/723 |

OTHER PUBLICATIONS

Cho, Myoungsu, "Stroscope: Multi-scale Visualization of Irregularly Measured Time-series Data"; Date: Feb. 26, 2014; 14 pages.
Fischer, Fabian, et al. "Vistracer: a visual analytics tool to investigate routing anomalies in traceroutes." Proceedings of the ninth international symposium on visualization for cyber security ACM 2012 8 pages.
Goodall, J.R. et al.; "Mathematics and Visualization"; VizSEC 2007, Proceedings of the Workshop on Visualization for Computer Securitydated: Jan. 2008, 28 pages.
Goodall, John R., "VIAssist: Visual Analytics for Cyber Defense." Technologies for Homeland Security, 2009. HST'09. IEEE Conference on. IEEE, 2009, 8 pages.
Hao Zhang; et al.,"SVM-KNN: Discriminative Nearest Neighbor Classification for Visual Category Recognition"; 2006; http://ieeexplore ieee org/stamp/stamp jsp?arnumber=1641014 2 pages.
Kastner, W. et al.; "Communication Systems for Building Automation and Control"; Jun. 2005; 29 pages.
Mansmann, Florian, et al. "Visual analysis of network traffic for resource planning, interactive monitoring, and interpretation of security threats." IEEE Transactions on Visualization and Computer Graphics 13 6 (2007): 1105-1112.
Rodrigues, J.F. et al.; "Visualization Tree, Multiple Linked Analytical Decisions"; University of Sao Paulo at Sao Carlos, dated: Jun. 10, 2005; 12 pages.
Roe, C.; "Sponsor Spotlight Column: ALTILIA on Big Data"; DATAVERSITY, Apr. 16, 2014; 7 pages.

* cited by examiner

Pseudo Code for Distance Calculation

402 — Input: Set of data records[] containing only categorical attributes, distance measure for every attribute, and a query object
404 — Output: all given data records[], ordered according to the distance to the query point for every record in data records do
    distance := 0;
    for every attribute a of record do
        406 — distance = distance + distance calculated using the distance measure for attribute a between the record and the query object
    endfor
    408 — distance = distance / number of attributes
    assign distance to record
endfor
410 — sort all records according to distance, ascending
return records

FIG. 4

| | 502 | 504 | | 506 | 508 | | | | 510 | | 512 | 514 | 416 | 524 |
|---|---|---|---|---|---|---|---|---|---|---|---|---|---|---|
| | art | y | | z | mrt | | src | spt | dst | dpt | Name | Proto | msg | |
| 3 | 3/26/2014 | 18:28 | 34744 | 13 | 3/26/2014 | 19:16 | 16.238.16.175 | 443 | 15.217.80.157 | 34744 | Teardown | TCP | A TCP connection between hosts was deleted | |
| 4 | 3/26/2014 | 18:28 | 34746 | 13 | 3/26/2014 | 19:16 | 16.238.16.175 | 443 | 15.217.80.157 | 34746 | Teardown | TCP | A TCP connection between hosts was deleted | |
| 5 | 3/26/2014 | 18:28 | 34748 | 13 | 3/26/2014 | 19:16 | 16.238.16.175 | 443 | 15.217.80.157 | 34748 | Teardown | TCP | A TCP connection between hosts was deleted | |

FIG. 5

| A | B | C | D | E | F | G | H | I | J | K | L | M | N | O | P | IY | IZ | JA | JB | JC | JD |
|---|---|---|---|---|---|---|---|---|---|---|---|---|---|---|---|----|----|----|----|----|----|
| eventid | end1 | mrt | ## | | dst | dpt | xxx | Name | yyy | aaa | aaa | bbb | ccc | ddd | eee | fff | ggg | hhh | iii | Dist | NormDist |
| ## | ## | ## | ## | 1 | 15.217.80.157 | 34744 | ## | | | | | | | | | | | | | 0 | 0 |
| ## | ## | ## | ## | 1 | 15.217.80.157 | 34746 | ## | | | | | | | | | | | | | 1 | 0.013889 |
| ## | ## | ## | ## | 1 | 15.217.80.157 | 34748 | ## | | | | | | | | | | | | | 1 | 0.013889 |
| ## | ## | ## | ## | 1 | 15.217.80.157 | 34750 | ## | | | | | | | | | | | | | 1 | 0.013889 |

FIG. 6A

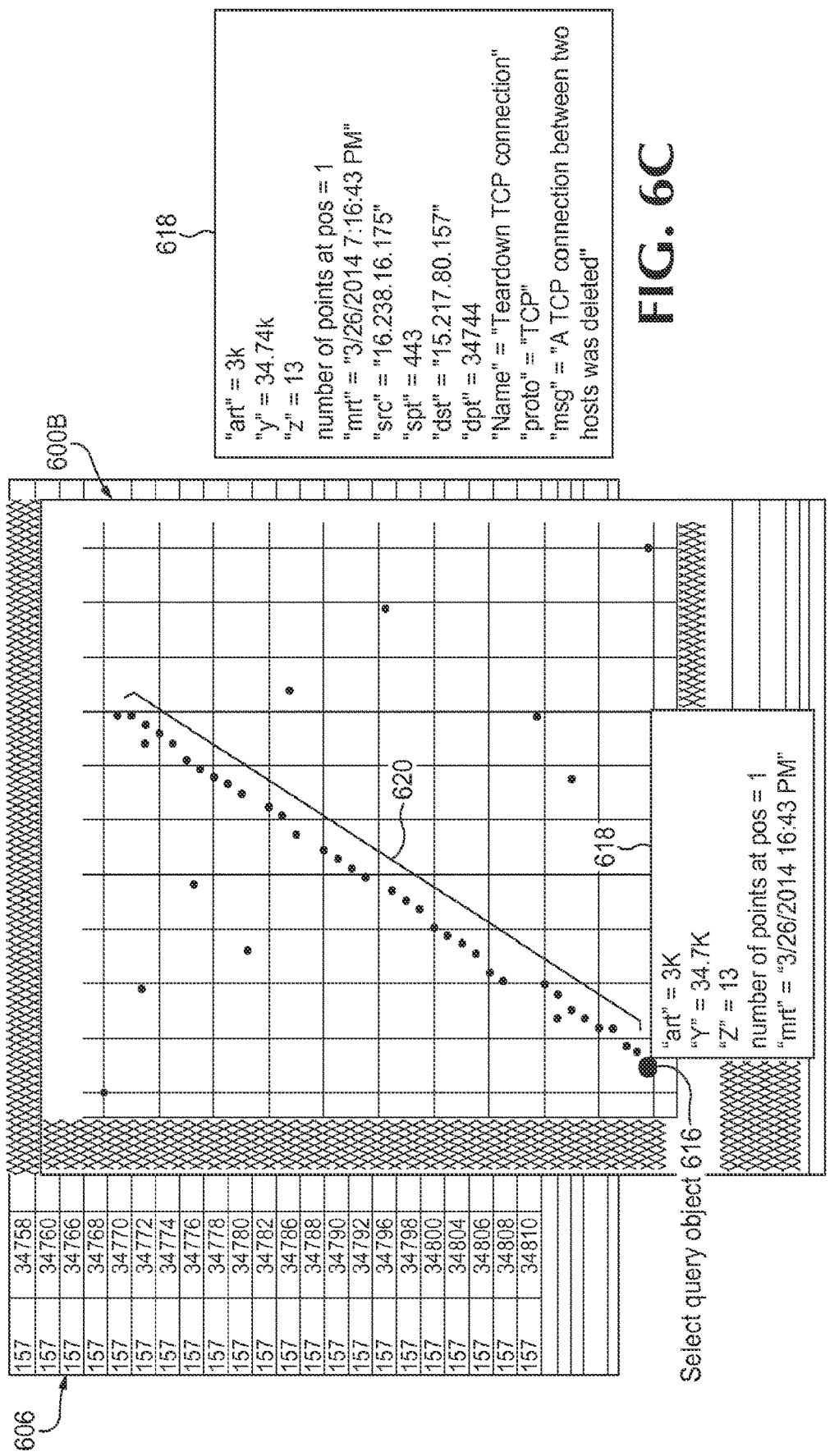

| | | | |
|---|---|---|---|
| 700 | 1 | Different | yyy.yyy.yyy.yyy and zzz.zzz.zzz.zzz |
| 702 | 0.75 | High distance | xxx.yyy.yyy.yyy and xxx.zzz.zzz.zzz |
| 704 | 0.5 | Average distance | xxx.xxx.yyy.yyy and xxx.xxx.zzz.zzz |
| 706 | 0.25 | Low distance | xxx.xxx.xxx.yyy and xxx.xxx.xxx.zzz |
| 708 | 0 | Same | xxx.xxx.xxx.xxx and xxx.xxx.xxx.xxx |

FIG. 7

SourceGeo location 800

| | EA | EB | EC | ED | EE | EF |
|---|---|---|---|---|---|---|
| 802 | slat | slong | sourceGeo | sourceGeo | sourceGeo | sourceGeo |
| 804 | 3.74E+11 | -1.22E+12 | 94304 | US | CA | Palo Alto |
| 806 | 2.50E+11 | 1.22E+12 | | TW | 3 | Taipei |
| | 3.04E+11 | -9.77E+11 | | US | | Austin |
| 808 | 3.04E+11 | -9.77E+11 | | US | | Austin |

FIG. 8

Device Vendor/Product 900

| | Device_Vendor | Device_Product | Device_Ve |
|---|---|---|---|
| | HP | DNSCap | 1 |
| | HP | DNSCap | 1 |
| | HP | DNSCap | 1 |
| | HP | DNSCap | 1 |
| | HP | DNSCap | 1 |
| | HP | DNSCap | 1 |
| 902 → | HP | DNSCap | 1 |
| | HP | DNSCap | 1 |
| 904 → | HP | DNSCap | 1 |
| | CISCO | FWSM | |
| 906 → | CISCO | FWSM | |

FIG. 9

ITERATIVE VISUALIZATION OF A COHORT FOR WEIGHTED HIGH-DIMENSIONAL CATEGORICAL DATA

BACKGROUND

Domain expert data analysts, such as market analysts, network security hunters, search for similar categorical data elements (i.e., a class of customer, a sequence of network events) to a given query object (i.e., a customers, an IP address) in a high dimensional data space.

BRIEF DESCRIPTION OF HE DRAWINGS

FIG. 4 is an example pseudo code illustrating an algorithm for determining the weighted similarity score.

FIG. 5 is an example of a high-dimensional categorical cyber security data.

FIG. 6A illustrates an example determination of weighted similarity scores.

FIG. 6B illustrates a visual representation 600B of categorical data elements.

FIG. 6C illustrates a blow-up of an example pop-up window of FIG. 6B.

FIG. 7 is an example association of weights with a degree of difference for categorical components based on IP addresses.

FIG. 8 illustrates an example association of weights with a degree of difference for categorical components based on geolocation.

FIG. 9 illustrates an example association of weights with a degree of difference for categorical components based on device vendor.

DETAILED DESCRIPTION

Figure 1:
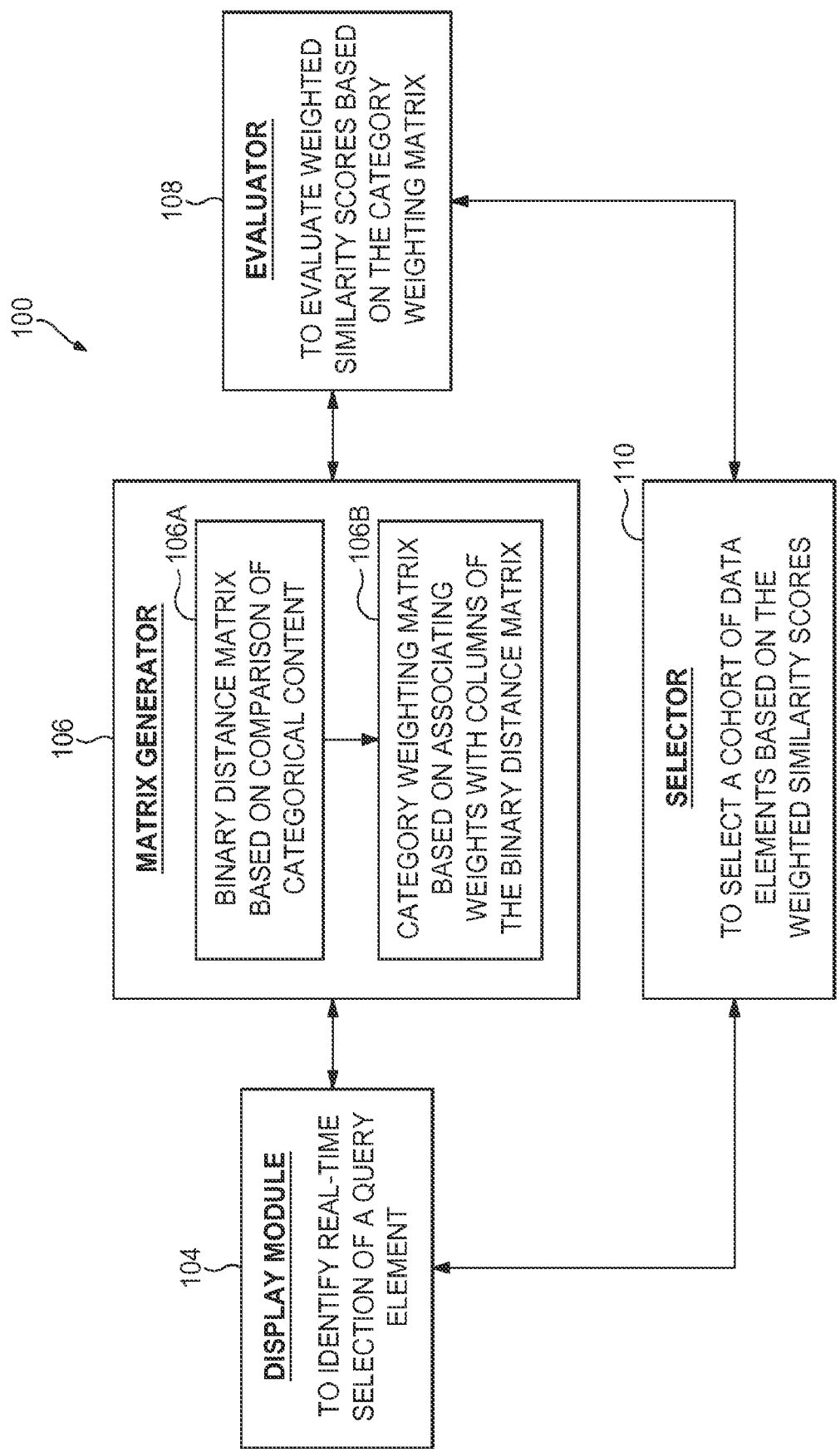
FIG. 1 is a functional block diagram illustrating one example of a system for iterative visualization of a cohort for weighted high-dimensional categorical data.

An important task for many big data applications such as in recommendation systems, predictive modeling, and pattern recognition, is a search for categorical data elements similar to a query object. A categorical data element is a data element (e.g., a high-dimensional data element) that comprises a plurality of categorical components (e.g., each dimension is a categorical component), where the categorical component is a value associated with a category. For example, in the area of cyber-security, data elements may include features related to operating system, Internet Protocol ("IP") address, packet size, port number, etc., and a categorical data element may be a high-dimensional vector comprising a plurality of categorical components or values for the features such as IP address, packet size, port number, etc.

Real world use cases for a search for categorical data elements similar to a query object may include, for example, a cyber-security visual analysis to find the common behaviors of security port scan events from a single security attack event. As another example, a market analyst may want to find customers with similar shopping behaviors. Real world use cases may also include, for example, methods for gaining and retaining customers and identifying groups of customers to focus on.

Existing methods of finding a cohort generally include applying various data mining methods on numerical data space with clustering, determining a Euclidian distance on a group of people, and so forth. However, in the real world, data may not be numerical. Instead, it may be large categorical data in a high dimensional space. Also, in many examples, instead of identifying a group of people, it may be useful to find a sequence of events, such as, for example, in cyber security space. Events may occur in different IP addresses, ports, geographical destinations, etc. If an attack event occurred, security hunters may want to identify other events similar to the one that occurred.

Existing techniques to find cohorts utilize multidimensional scaling ("MDS") and principle component analysis ("PCA"). The techniques disclosed herein compute numerical distance via a frequency count. Also, for example, the techniques disclosed herein include associating similarity weights to each category to determine a degree of similarity. For example, a higher weight may he associated with two IP addresses that are in the same subnet, and a lower weight may be associated with two IP addresses that are in different subnets. Such weights may be adjusted and/or refined by a user to identify cohorts that are more suitable for a particular purpose.

As described herein, a pixel-based workflow is disclosed to allow users (e.g., domain experts) to find nearest neighbors (cohort, objects with similar dimensions) to a query object in a high-dimensional categorical data space where each pixel represents an event. In some examples, a color may represent a value of a dimension. The workflow is iterative and interactive, combining automatic interestingness measures with human domain knowledge to find a nearest neighbor to a query object in a high dimensional categorical space on system events (i,e., pixels, cyber security events, vs. a group of people). In some examples disclosed herein, users may be allowed to add weights to adjust results from a binary operation (i.e., 0, and 1) on an attribute (or dimension). Applying weights to results from the binary operation make a better similarity comparison between each event with the query object for users to refine their hypothesis. Nearest neighbor cohorts may be selected based on the weighting factors. In some examples, users may adjust the weighting factors to generate a list of similar events (cohort) to meet their needs.

Search of numerical and/or categorical data may be facilitated by an application of various statistical methods to features of the data. However, as disclosed herein, the end-user is allowed to provide meaningful input during the search process (e.g., by providing weights), which allows for screening of a large number of dimensions/categories/categorical components (events/pixels) at scale. Also, for example, such information is provided to the user so that it may be meaningfully understood how and why such results are obtained. As another example, as disclosed herein, selection of attributes may be tuned to an individual query object so that the selection of nearest neighbors may be relevant to that query object.

This disclosure provides iterative techniques combined with a binary distance matrix with an iterative weighting factor selection, to enable users to perform visually driven cohort analysis in a high dimension space.

As described in various examples herein, iterative visualization of a cohort for weighted high-dimensional categorical data is disclosed. One example is a system including a display module, a matrix generator, an evaluator, and a selector. The display module identifies real-time selection of a query data element in an interactive visual representation of high-dimensional categorical data elements comprising a plurality of categorical components. The matrix generator generates a binary distance matrix with columns representing the plurality of categorical components, and entries in a row indicative of a degree of similarity of respective categorical components of the selected query data element to a data element represented by the row, and determines a category weighting matrix by associating a weight with entries in each column of the binary distance matrix. The evaluator evaluates a weighted similarity score for a data element represented by a row of the category weighting matrix based on entries of the row. The selector iteratively and interactively selects, based on weighted similarity scores, a cohort of categorical data elements for the query data element.

In the following detailed description, reference is made to the accompanying drawings which form a part hereof, and in which is shown by way of illustration specific examples in which the disclosure may be practiced. It is to be understood that other examples may be utilized, and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

FIG. 1 is a functional block diagram illustrating one example of a system 100 for iterative visualization of a cohort for weighted high-dimensional categorical data. System 100 is shown to include a display module 104, a matrix generator 106, an evaluator 108, and a selector 110. In some examples, the display module 104 may be communicatively linked to an interactive graphical user interface (not illustrated in FIG. 1).

The term "system" may be used to refer to a single computing device or multiple computing devices that communicate with each other (e.g. via a network) and operate together to provide a unified service. In some examples, the components of system 100 may communicate with one another over a network. As described herein, the network may be any wired or wireless network, and may include any number of hubs, routers, switches, cell towers, and so forth. Such a network may be, for example, part of a cellular network, part of the internet, part of an intranet, and/or any other type of network.

Figure 2:
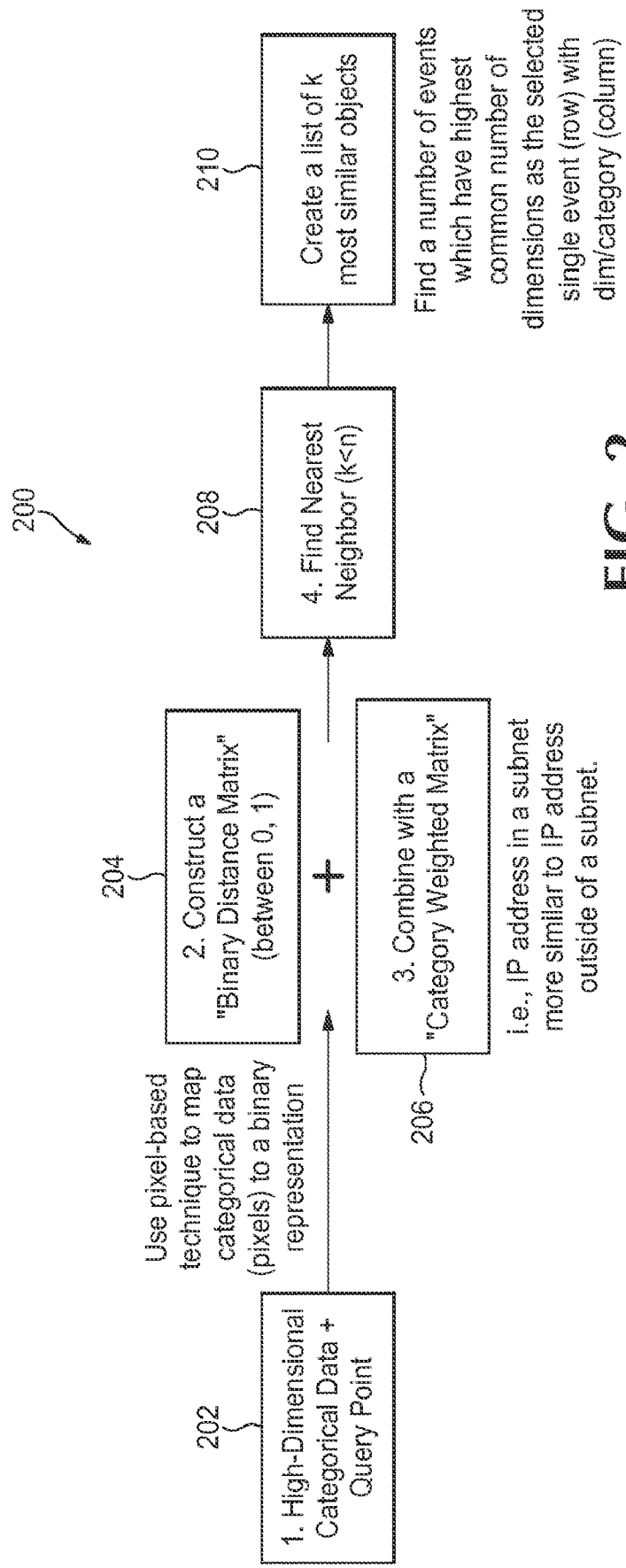
FIG. 2 is an overview of an example visual analytics workflow.

FIG. 2 is an overview of an example visual analytics workflow. At 202, high-dimensional categorical data and a query point may be identified via an interactive graphical representation. In some examples, a pixel-based technique may be utilized to visually represent each categorical data element via a pixel. At 204, a binary distance matrix may be constructed to represent the high-dimensional categorical data. The binary distance matrix may include numerical entries between 0 and 1. For example, a row of the binary distance matrix may be associated with a categorical data element, and each column may represent an attribute or category of the data elements. At 206, a category weighting matrix may be determined where each column (or attribute, category) of the binary distance matrix is associated with a weight. For example, if a category represents IP addresses, then weights may be associated with the category such that two IP addresses that are in a subnet are associated with higher weights than two IP addresses that are not in the same subnet. At 208, k-nearest neighbors of n data elements may be selected. At 210, a list of k most similar data items may be created. These, and other aspects of the example visual analytics workflow system will be described in detail with respect to system 100 of FIG. 1.

Referring again to FIG. 1, the display module 104 may identify real-time selection of a query data element in an interactive visual representation of high-dimensional categorical data elements comprising a plurality of categorical components. Generally, the high-dimensional categorical data elements describe contents of a high-dimensional dataset. In some examples, the high-dimensional categorical data elements may be a cyber-security log file, proxy data, Web navigation logs (e.g. click stream), and healthcare data.

In some examples, the visual representation may include a representation of each data element by a pixel. For example, the categorical data elements may be represented graphically, where each pixel in the graph represents a data element. Also, for example, the categorical data elements may represent IP addresses that are logged into a secured network during a time interval, and the visual representation may be a graphical representation of the IP addresses, where each data pixel represents a record of an IP address.

In some examples, a pixel attribute associated with the pixel may represent a characteristic of the data element represented by the pixel. For example, the pixel attribute may be color, and a color scheme may be associated with a data element. In some examples, a color may be associated with an IP address, and each pixel representing the IP address may be associated with the respective color. In some examples, each pixel may represent a range of IP addresses and a color may be associated with the range.

A "real-time selection" as used herein generally refers to a selection of a query data element while a user interacts with the interactive visual representation in real time. For example, each pixel in the interactive visual representation may represent a categorical data element, and the user may select a data element by clicking on a pixel. The display module 104 may identify selection of the data element by identifying the click on the pixel.

Figure 3A:
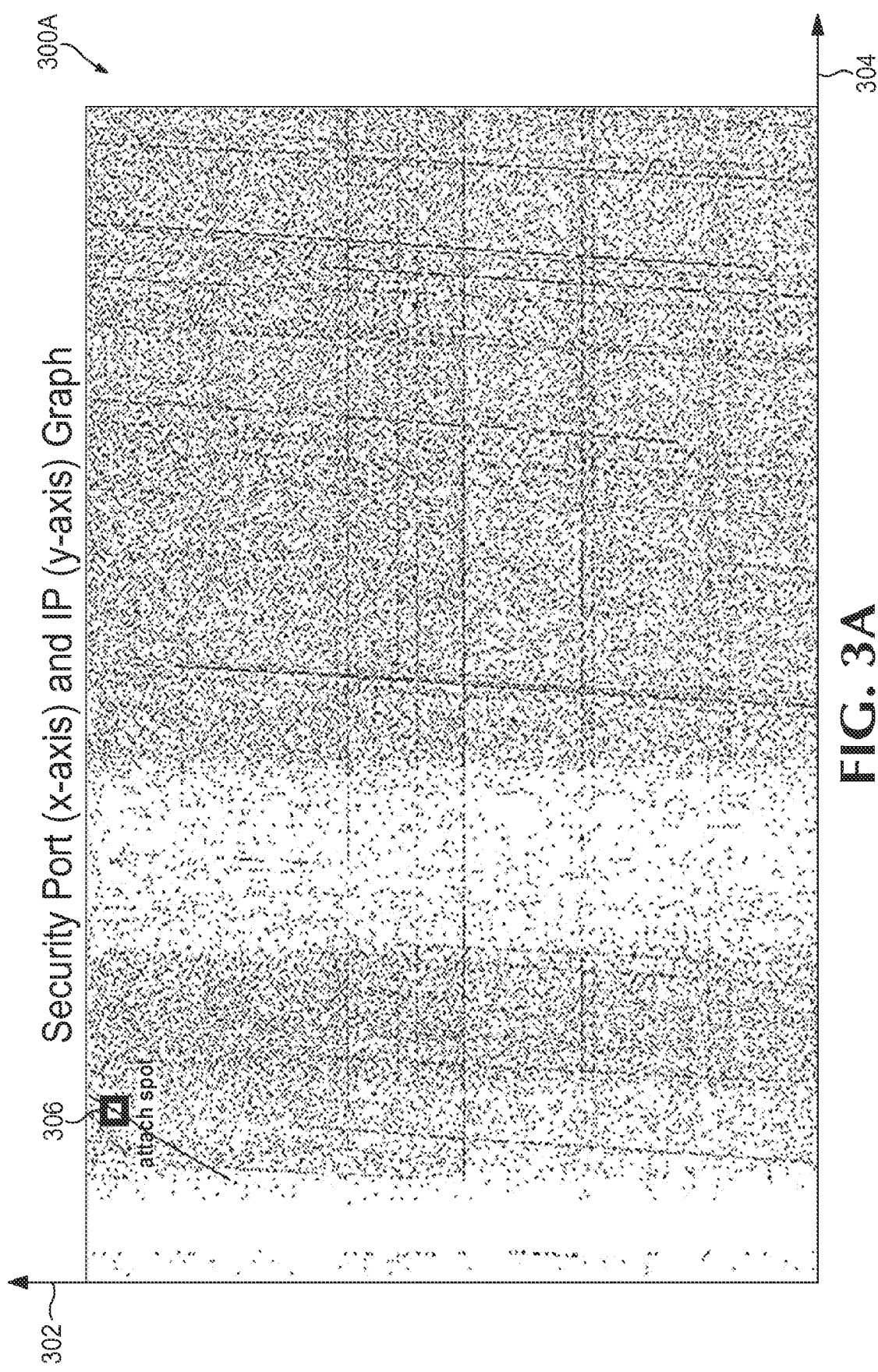
FIG. 3A is an example of a visual representation of high-dimensional categorical data elements.

FIG. 3A is an example of a visual representation of high-dimensional categorical data elements. For example, a high volume complex security port graph 300A is illustrated. As illustrated, in some examples, a given data element of the high-dimensional categorical data elements may be a pair comprising an IP address and a port number. The horizontal axis 304 may represent security port number, and the vertical axis 302 may represent IP address. In some examples, color of a pixel may represent a numerical value of an IP address. Each pixel may represent a categorical data element with over 261 dimensions (or attributes, categories, or categorical components), such as, IP address, port, protocol, and so forth. A query data element, representative of a suspicious attack event, may be identified in an attack spot 306. In some examples, the visual representation 300A may include a billion rows of events, each represented by a pixel, and each event including over 261 dimensions.

Figure 3B:
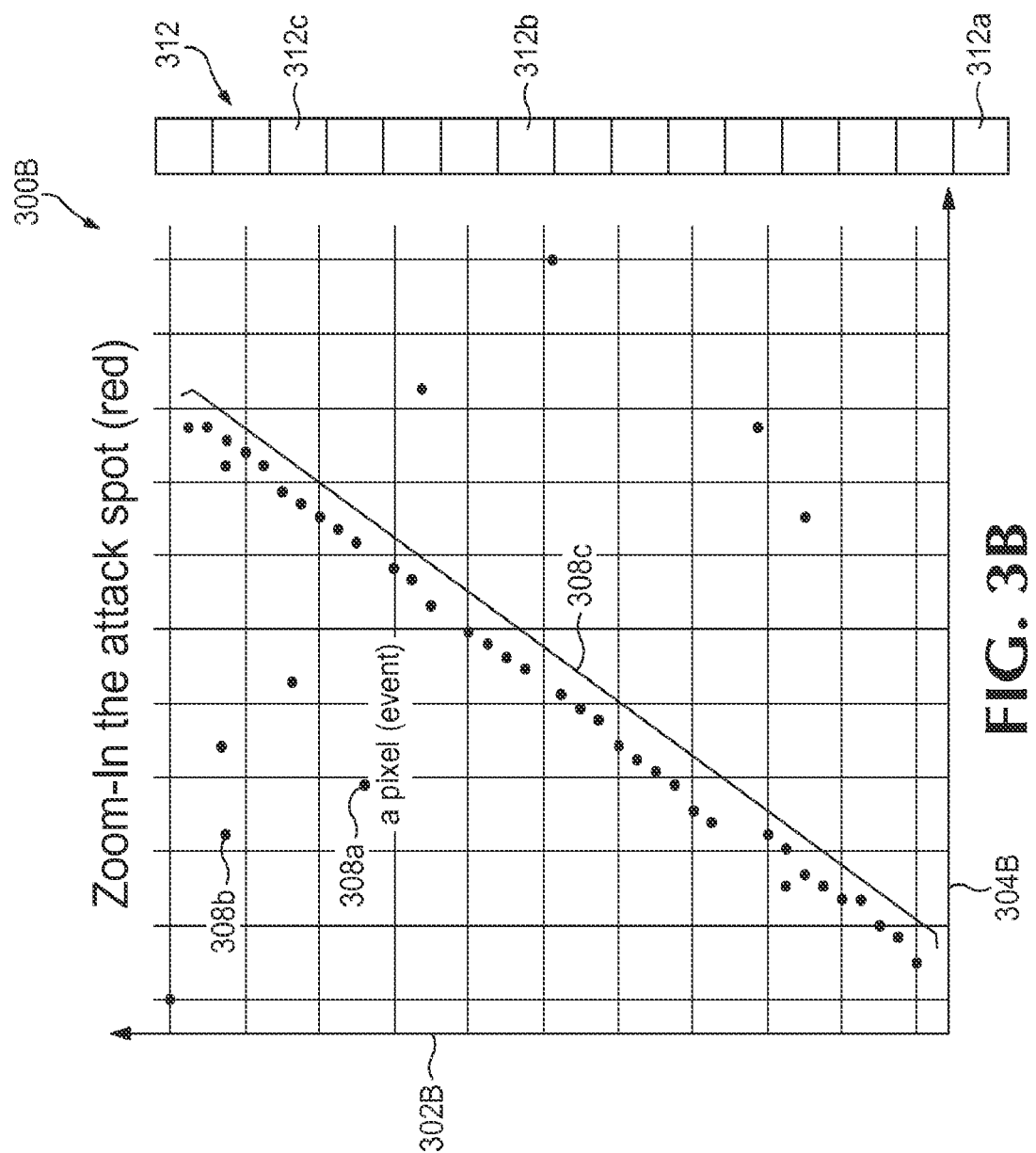
FIG. 3B is an example zoom-in pixel scale map of an example attack spot illustrated in FIG. 3A.

FIG. 3B is an example zoom-in pixel scale map 300B of an example attack spot 306 illustrated in FIG. 3A. As illustrated, the pixel scale map 300B is a zoom-in display of the example attack spot 306 illustrated in FIG. 3A. The horizontal axis 304B may represent a security port number, and the vertical axis 302B may represent an IP address. In some examples, color of a pixel may represent a numerical value of an IP address. As illustrated, each data element may be represented by a pixel, and a color spectrum 312 may be utilized to represent IP addresses. A suspicious attack event 308a is illustrated. In some examples, attack event 308a may be associated with a first color 312a (e.g., red) in the color spectrum 312. Color spectrum 312 may describe colors based on weighted similarity scores (as described herein). For example, a second color 312b may represent a data element 308b that is more similar to the data element corresponding to the attack event 308a, whereas a third color 312c may represent diagonally positioned data elements 308c that are less similar to the data element corresponding to the attack event 308a.

Referring again to FIG. 1, the display module 104 may communicate with the interactive graphical user interface to interact with a user. For example, a user may select and zoom into a suspected attack spot (e.g. attack spot 306 in FIG. 3A). Based at least in part on such selection, a series of interactions may be performed via the display module 104. For example, hovering over a data element (event) may display contents of the data element, drilldown may be performed for further analysis, and a query cohort may be selected for searching similar attack events.

The matrix generator 106 may generate a binary distance matrix 106A with columns representing the plurality of categorical components, and entries in a row indicative of a degree of similarity of respective categorical components of the selected query data element to a data element represented by the row. Generally, the first row in the binary distance matrix 106A may represent the selected query data element, and each successive row in the binary distance matrix 106A may represent a data element. In some examples, a matrix entry 0 may represent identical categorical components, and 1 may represent non-identical categorical components. For example, if the IP address associated with a given categorical data element is the same as the IP address associated with the query data element, then the corresponding column entry (representing IP address) in the binary, distance matrix 106A may be 0. Likewise, if the IP address associated with the given categorical data element is different from the IP address associated with the query data element, then the corresponding column entry (representing IP address) in the binary distance matrix 106A may be 1.

Further, the matrix generator 106 may determine a category weighting matrix 106B by associating a weight with entries in each column of the binary distance matrix. Weights may be utilized to define a degree of importance (e.g., distance of criteria from the query object). In some examples, the matrix entry 1 is substituted with a value between 0 and 1, the value indicative of a degree of difference of the non-identical content. For example, if the IP address associated with the given categorical data element is different from the IP address associated with the query data element, but the IP addresses belong, to the same subnet, then the corresponding weight for the column entry (representing IP address) in the binary distance matrix 106A may be a numerical value less indicative of a degree of difference of the non-identical content than if the IP addresses belong to different subnets. For example, a query data element with an IP address 16.210.1112 may have less distance with a given data element with an IP address 16.210.131.60 than another data element with an IP address 15.217.80.15 because 16.210.1112 and 16.210.131.60 are in the same subnet.

In some examples, the matrix generator 106 may determine the category weighting matrix via an iterative and interactive process based on weights received from a user, the weights associated with a relevance of the categorical component represented by the column. Assigning meaning to weights is generally subjective and may require application domain knowledge. Accordingly, in some examples, input on the weights for some dimensions may he received from a user. For example, the user may assign weights based on relevance, to the user, of results of the cohort analysis. Accordingly, the user may be able to exercise control over identifying a similar cohort.

The evaluator 108 may evaluate a weighted similarity score for a data element represented by a row of the category weighting matrix based on entries of the row, in some examples, the weighted similarity score for the data element is normalized based on a sum of entries of the row in the category weighting matrix divided by the number of categorical components.

FIG. 4 is an example pseudo code illustrating an algorithm for determining the weighted similarity score. At 402, input to the algorithm may include a set of data records containing categorical attributes (e.g., high-dimensional categorical data elements, each data element comprising a plurality of categorical components), a distance between categorical components, and a query data element. At 404, output of the algorithm may include all the input data records, ranked according to their respective weighted similarity scores.

The weighted similarity score, or distance, may be initialized to 0. At 406, the weighted similarity score, or distance, is inductively summed. Each categorical component with an input distance 1 may contribute to the sum. At 408, the weighted similarity score may be normalized by dividing the weighted similarity score obtained at 406, by the total number of attributes (or categories or categorical components). Such a normalized weighted similarity score is associated with a given data record, or categorical data element. At 410, the input data records may be sorted based on their respective scores. In some examples, the sorting may be performed in an ascending order of weighted similarity scores.

FIG. 5 is an example of a high-dimensional categorical cyber security data 500. In some examples, security data 500 may include categorical data elements comprising a plurality of categorical components, for example, with 260 dimensions or categorical components. A blow-up 524 of rows 3, 4, and 5 is illustrated. Categorical component 502 represents "art" which may be the dater and/or time of an event (a data element). Categorical component 504 represents "y" which may be a port number. Categorical component 506 represents "mrt" which may be another time stamp. Categorical component 508 represents "src" which may be an IP address. Categorical component 510 represents "dst" which may be another IP address. Categorical component 512 represents "Name" which may be a name associated with the event, such as, for example, "Teardown", "Blacklisted", "Deny inbound", and so forth. Categorical component 514 represents "proto" which may be a protocol associated with the event, such as, for example, "TCP", "UDP", and so forth. Categorical component 516 represents "msg" which may be a message associated with the event, such as, for example, "A TCP connection between two hosts was deleted".

FIG. 6A illustrates an example determination of weighted similarity scores. Generally, as used herein, distance and weighted similarity score may be used interchangeably. Likewise, normalized distance and normalized weighted similarity score may be used interchangeably. As illustrated, a query data element 602 may be selected in a visual representation 600. Hovering over (e.g., with a mouse) the query data element 602 may cause a pop-up window 604 to appear with details of the query data element 602. The pop-up window 604 may display the plurality of categorical components for the query data element 602, such as, for example, "Art=3.222M, Y=44K, Z=10, Number of points at pos=14, Mrt=3/26/2014 7:15:35 PM"

A binary distance matrix may be associated with the categorical data items displayed in the visual representation 600. In some examples, the high-dimensional data elements may be represented in an excel file format 606, with rows corresponding to data elements and columns corresponding to categorical components. For example, the second row 608 may be associated with the query data element 602. In some examples, the data in the second row 608 may be provided in the pop-up window 604.

Also, for example, column 610 titled "JC", may represent a weighted similarity score (or distance "Dist") between the query data element 602 and a given data element. As illustrated, the weighted similarity score between the query data element 602 with itself is 0. Likewise, the weighted similarity score between the query data element 602 with another data element 612 is 1 because the only categorical component in which the query data element 602 and the data elements 612 are different is "dpt" in column G 614. For the query data element 602, dpt=34744, whereas for each of the data elements 612, dpt=34752. Also, as illustrated, the IP addresses (or "dst") for the query data element 602 and the data elements 612 are identical, as illustrated in column F 614A is "15.217.80.157". All other categorical components are identical. Accordingly, the weighted similarity score is 1.

Also, for example, column 610A titled "JD", may represent a normalized weighted similarity score (or normalized distance, "NormDist") between the query data element 602 and a given data element of the data elements 612. In some examples, there may be 72 categorical components and the query data element 602 may differ from the given data element of the data elements 612 in 1 categorical component. Accordingly, each such categorical component may be associated with a matrix entry of 1 in column JC 610 for the weighted similarity score, and the sum of the entries of the row add up to 1. A normalized weighted similarity score may be determined by taking the sum and dividing by the number of categorical components, i.e. 1/72=0.013889, as illustrated in column 610A.

FIG. 6B illustrates a visual representation 600B of categorical data elements. As illustrated, another query data element 616 may be selected in the visual representation 600B. Visual representation 600B also illustrates diagonal data elements 620 that are similar to the selected query data element 616. Hovering over (e.g., with a mouse) the selected query data element 616 may cause a pop-up window 618 to appear with details of the selected query data element 616. The pop-up window 618 may display the plurality of categorical components for the selected query data element 616, for example, "Art=3K, Y=34.7K, Z=13, Number of points at pos=1, Mrt=3/26/2014 16:43 PM". In some examples, the high-dimensional data elements may be represented in an excel file format 606, with rows corresponding to data elements and columns corresponding to categorical components.

FIG. 6C illustrates a blow-up of an example pop-up window 618 of FIG. 6B. The pop-up window 618 may display categorical components for the selected query data element 616. In some examples, data from a corresponding row for the selected query data element 616 in the excel file format 606 may be associated with the selected query data element 616. In some examples, the data in the corresponding row may be provided in the pop up window 618. For example, the categorical components may include "art" = 3K, "y" =34.74K, "z" =13, number of points at pos=1, "mrt"="3/26/2014 7:16:43 PM", "src"="16.238.16.175", "spt"=443, "dst"="15.217.80.157", "dpt"=34744, "Name"="Teardown TCP connection", "proto"="TCP", "msg"="A TCP connection between two hosts was deleted", and so forth. Data elements similar to the selected query data element 616 may be represented as diagonal data elements 620. As illustrated, diagonal data elements 620 may be associated with an event corresponding to a "Teardown TCP connection" with a message "A TCP connection between two hosts was deleted". A user searching for events similar to the event represented by the selected query data element 616 may be presented with similar events represented by the diagonal data elements 620. The user may then iteratively select a data element of the diagonal data elements 620 for further analysis. The user may also hover over a data element of the diagonal data elements 620 to view a pop-up window displaying features of similar events. For example, the user may view event times (provided as "mrt"), and so forth.

As described herein, in some examples, a user may input weights for categorical components via the display module 104 of FIG. 1. In some examples, the matrix generator 106 of FIG. 1 may determine the category weighting matrix via an iterative and interactive process based on weights received from the user, where the weights may be associated with a relevance of the categorical component represented by a column of the binary distance matrix 106A and/or the category weighting matrix 106B. In some examples, the categorical components may include 1P address, port number, geolocation, and protocol. In some examples, weights may be associated with an IP address, port number, geolocation, and/or protocol.

FIG. 7 is an example association of weights with a degree of difference for categorical components based on IP addresses. For example, at 700, a weight "1" may be associated with IP addresses that are "Different" such as yyy.yyy.yyy.yyy and zzz.zzz.zzz.zzz. For example, when comparing IP addresses, a first IP address "15.217.80.157" and a second IP address "16.220.81.160" have different values, and may be associated with a weight "1" associated with "Different". In some examples, the user may input such a weight via the display module 104 of FIG. 1.

At 702, a weight "0.75" may be associated with IP addresses that have a "High distance" such as xxx.yyy.yyy.yyy and xxx.zzz.zzz.zzz. For example, when comparing IP addresses, a first IP address "15.217.80.157" and a third IP address "15.220.81.160" are identical in the first subnet value but differ in the last three values, and may be associated with a weight "0.75" associated with a "High distance".

At 704, a weight "0.5" may be associated with IP addresses that have an "Average distance" such as xxx.xxx.yyy.yyy and xxx.xxx.zzz.zzz. For example, when comparing IP addresses, a first IP address "15.217.80.157" and a fourth IP address "15.217.81.160" are identical in the first two subnet values but differ in the last two values, and may be associated with a weight "0.5" associated with an "Average distance".

At 706, a weight "0.25" may be associated with IP addresses that have "Low distance" such as xxx.xxx.xxx.yyy and, xxx.xxx.xxx.zzz. For example, when comparing IP addresses, a first IP address"15.217.80.157" and a fifth IP address "15.217.80.160" are identical in the first three subnet values but differ in the last value, and may be associated with a weight "0.25" associated with a "Low distance".

At 708, a weight "0" may be associated with IP addresses that are the "Same" such as xxx.xxx.xxx.xxx and xxx.xxx.xxx.xxx. For example, when comparing IP addresses, a first IP address "15.217.80.157" and a sixth IP address "15.217.80.157" are identical, and may be associated with a weight "0".

FIG. 8 illustrates an example association of weights with a degree of difference for categorical components based on geolocation. Source geolocation 800 may illustrate data indicative of a geolocation for a source of a data element. At 802, column EA may be indicative of source latitude ("slat"), column EB may be indicative of source longitude ("slong"), column EC may be indicative of source location such as a zip code, column ED may be indicative of source location such as a country, column EE may be indicative of source location such as a state, and column EF may be indicative of source location such as a city.

In some examples, weights may be associated with a degree of difference for categorical components based on geolocation. For example, comparison of columns ED and EF indicate that data element 804 and data element 808 are representative of the same source for country ("USA"), but different sources for cities ("Palo Alto" and "Austin", respectively), and may be associated with a weight indicative of a low distance. However, data element 806 is representative a source for a country ("Taiwan" or "TW") different from USA, and may be associated with a weight indicative of a high distance. As described herein, in some examples, a user may input such weights via the display module 104 of FIG. 1.

FIG. 9 illustrates an example association of weights with a degree of difference for categorical components based on device vendor. Source data for device vendor/product 900 may be data indicative of a vendor and/or product. For example, comparison of device vendors associated with data element 902 and data element 904 may indicate that the respective data elements are representative of the same vendor "HP". Accordingly, data element 902 and data element 904 may be associated with a weight indicative of a low distance. However, data element 906 is indicative of a vendor "Cisco" that is different from vendor "HP", and may be accordingly associated with a weight indicative of a high distance. As described herein, in some examples, a user may input such weights via the display module 104 of FIG. 1.

Referring again to FIG. 1, the selector 110 may iteratively and interactively select, based on weighted similarity scores, a cohort of categorical data elements for the query data element. For example, a list of k most similar events to a single selected query data element may be created. In some examples, the cohort of categorical data elements may comprise data elements similar to the query data element. The phrase "iteratively and interactively select" as used herein, generally refers to an iterative process of selecting the cohort based on interactions with a user. For example, the user may modify the cohort iteratively via an interactive graphical user interface.

In some examples, the cohort of categorical data elements may comprise data elements not similar to the query data element. For example, system 100 may provide a user with tools for an interactive and iterative validation of the cohort of categorical data elements, where the validation may include receiving, from a user, an indication to modify the cohort based on the weighted similarity scores. For example, display module 104 may provide the cohort of categorical data elements via an interactive graphical user interface, and the tools for an interactive and iterative validation of the cohort of categorical data elements may include a user interactive dissimilarity map for result validation. In some examples, the user may navigate the interactive dissimilarity map to learn the similarity/dissimilarity among different dimension and to validate the cohort results.

In some example, the indication to modify may include one of an indication to add a data element to the cohort and an indication to remove a data element from the cohort. For example, the user may indicate, via the display module 104, that a data element included in the cohort may be removed. Likewise, the user may indicate, via the display module 104 that a data element not included in the cohort may be included, In some examples, such inclusion and/or removal of a data element may be a consequence of weights associated with the categorical components. For example, the user may review the cohort selected by selector 110 and displayed by display module 104. The user may iteratively vary the weights associated with data elements in the displayed cohort and/or data elements not in the displayed cohort, and provide such weights via the display module 104. The display module 104 may provide the weights to the matrix generator 106 to determine an updated binary distance matrix 106A and/or category weighting matrix 106B. The evaluator may then evaluate updated weighted similarity scores, and the selector 110 may select an updated cohort, and the display module 104 may provide the updated cohort to the user. As described herein, the cohort may be iteratively and interactively modified by the user.

In some examples, such an iterative and interactive cohort selection may be performed to identify data patterns of interest to a user, such as a domain expert. A domain may be an environment associated with the high-dimensional categorical data elements, and domain relevance may be semantic and/or contextual knowledge relevant to aspects of the domain. For example, the high-dimensional categorical data elements may be related to customer transactions, and the domain may be a physical store where the customer transactions take place, and domain relevance may be items purchased at the physical store and the customer shopping behavior. As another example, the high-dimensional categorical data elements may be representative of Web navigation logs (e.g. click stream), and the domain may be the domain name servers that are visited via the navigation logs, and domain relevance may be analysis of internet traffic. Also, for example, the high-dimensional categorical data elements may be related to operational or security logs, and the domain may be a secure office space for which the security logs are being maintained and/or managed, and domain relevance may be tracking security logs based on preferences such as location, time, frequency, error logs, warnings, and so forth.

Generally, a domain expert may be an individual in possession of domain knowledge. For example, the domain may be a retail store, and the domain expert may be the store manager. Also, for example, the domain may be a hospital, and the domain expert may be a member of the hospital management staff. As another example, the domain may be a casino, and the domain expert may be the casino manager. Also, for example, the domain may be a secure office space, and the domain expert may be a member of the security staff.

In some examples, the high-dimensional categorical data elements may be security big data including a number of data elements (e.g., including 15, 936 data elements), and each data element may comprise a number of dimensions (e.g., 500 dimensions or categorical components). In some examples, product similarity comparison, healthcare patient, and market customer data may be analyzed to select cohorts in respective high dimensional categorical data spaces.

Figure 10A:
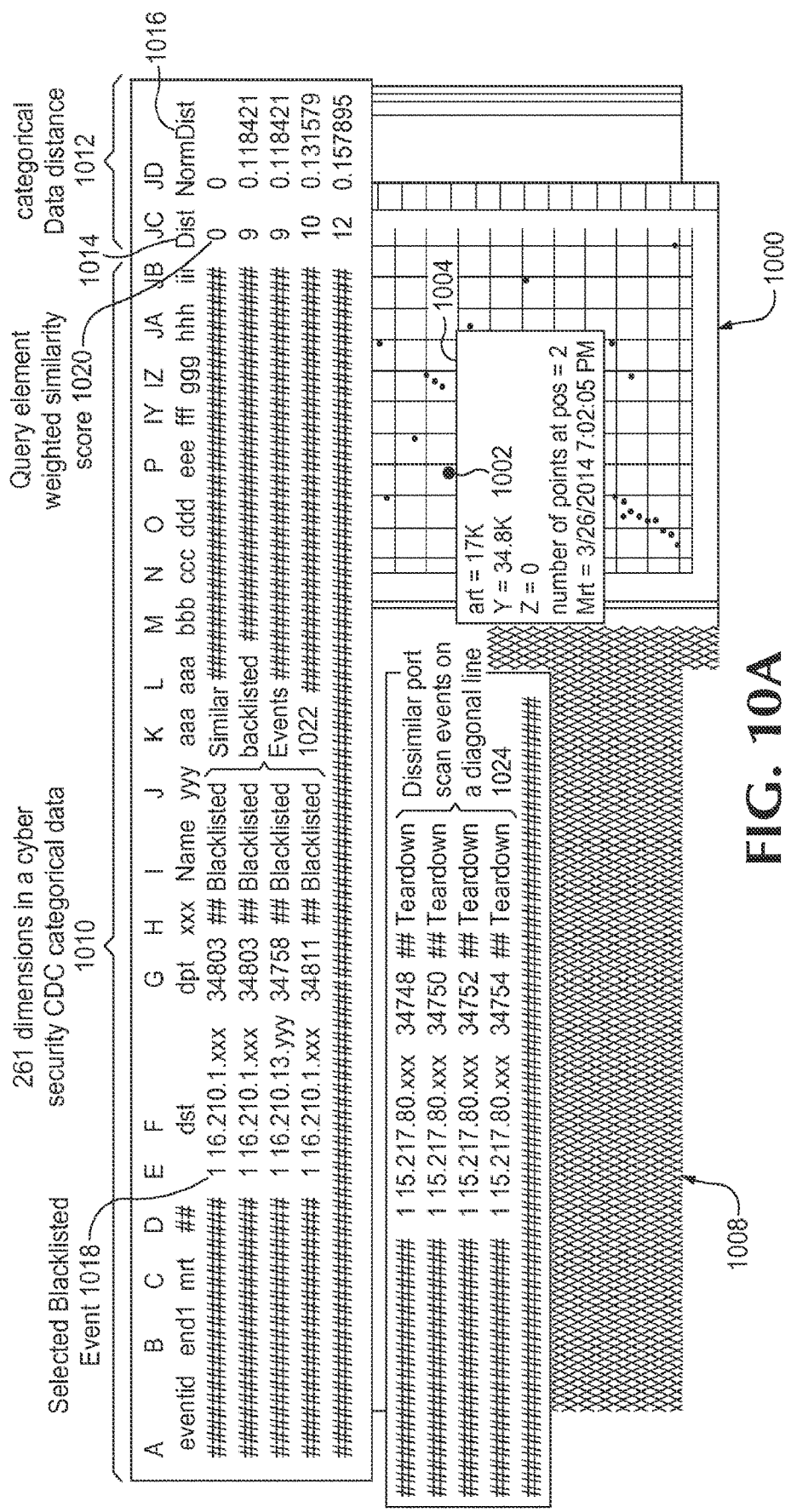
FIG. 10A illustrates an example of highlighting a visual representation of data elements of interest.

FIG. 10A illustrates an example of cohort selection for a query data element 1020. Some aspects of FIG. 10A may be similar to aspects of system 100 described in FIG. 6A. The high-dimensional categorical data elements may each comprise 261 dimensions or categorical components from a cyber-security environment. As illustrated, a cohort search for "blacklisted Name" may be performed. In some examples, two cohorts may be selected. As illustrated, a query data element 1002 may be selected in a visual representation 1000. Hovering over (e.g., with a mouse) the query data element 1002 may cause a pop-up window 1004 to appear with details of the query data element 1002. The pop-up window 1004 may display the plurality of categorical components for the query data element 1002, for example, "Art=17K, Y=34.8K, Z=0. Number of points at pos=2, Mrt=3/26/2014 7:02:05 PM".

A binary distance matrix may be associated with the categorical data items displayed in the visual representation 1000. In some examples, the high-dimensional data elements may be represented in an excel file format 1008, with rows corresponding to data elements and columns corresponding to categorical components. For example, query data element 1002 may be represented by the first row in the excel file format 1008. Query data element 1002 may be a selected "blacklisted" event 1018. As illustrated, the data displayed in the pop-up window 1004 may correspond to row entries in the first row in the excel file format 1008 representing the selected "blacklisted" event 1018.

Column 1014 provides the weighted similarity scores (or distances "Dist") for the data elements, where the weighted similarity scores are indicative of a distance of the data elements from the query data element 1002 (or the selected "blacklisted" event 1018). Column 1016 provides normalized weighted similarity scores (or normalized distances "NormDist"), based, for example, on the example algorithm illustrated in FIG. 4. As illustrated, the weighted similarity score 1020 (and the normalized weighted similarity score) for the query data element 1002 is 0. Entries for data elements in column 1014 that appear in the rows immediately after the weighted similarity score 1020 for the selected "blacklisted" event 1018 may have values in the range 9 through 24 (only values in the range 9 through 12 are illustrated in FIG. 10A), with respective normalized weighted similarity scores (in Column 1016) in the range 0.118421 to 0.315789 (only values in the range 0.118421 to 0.157895 are illustrated in FIG. 10A). Such data elements may be selected as a cohort of similar blacklisted events 1022. As illustrated, a categorical data distance 1012 may be the weighted similarity score (or distance) in Column 1014, and/or the normalized weighted similarity score (or normalized distance) in Column 1016.

After the similar blacklisted events 1022 are listed, the rows in the excel file format 1008 may represent dissimilar port scan events 1024. For example, normalized weighted similarity scores represented in Column 1016, may exceed 0.315789 by a threshold amount, thereby clearly demarcating the successive data elements with normalized weighted similarity scores greater than 0.315789 from the cohort of similar blacklisted events 1022 with respective normalized weighted similarity scores (in Column 1016) in the range 0.118421 to 0.315789. The successive data elements with normalized weighted similarity scores that exceed 0.315789 by a threshold amount may be identified as dissimilar port scan events 1024. It may be noted that the similar blacklisted events 1022 are similar to each other, and are similar to the selected blacklisted event 1018. However, the dissimilar port scan events 1024 are similar to each other, but are dissimilar from the selected blacklisted event 1018.

In some examples, the display module 104 of FIG. 1 may display the dissimilar port scan events 1024 along a diagonal in the visual representation 1000. Also, for example, the display module 104 of FIG. 1 may display the similar blacklisted events 1022 as a cluster of off-diagonal data points in the visual representation 1000.

Figure 10B:
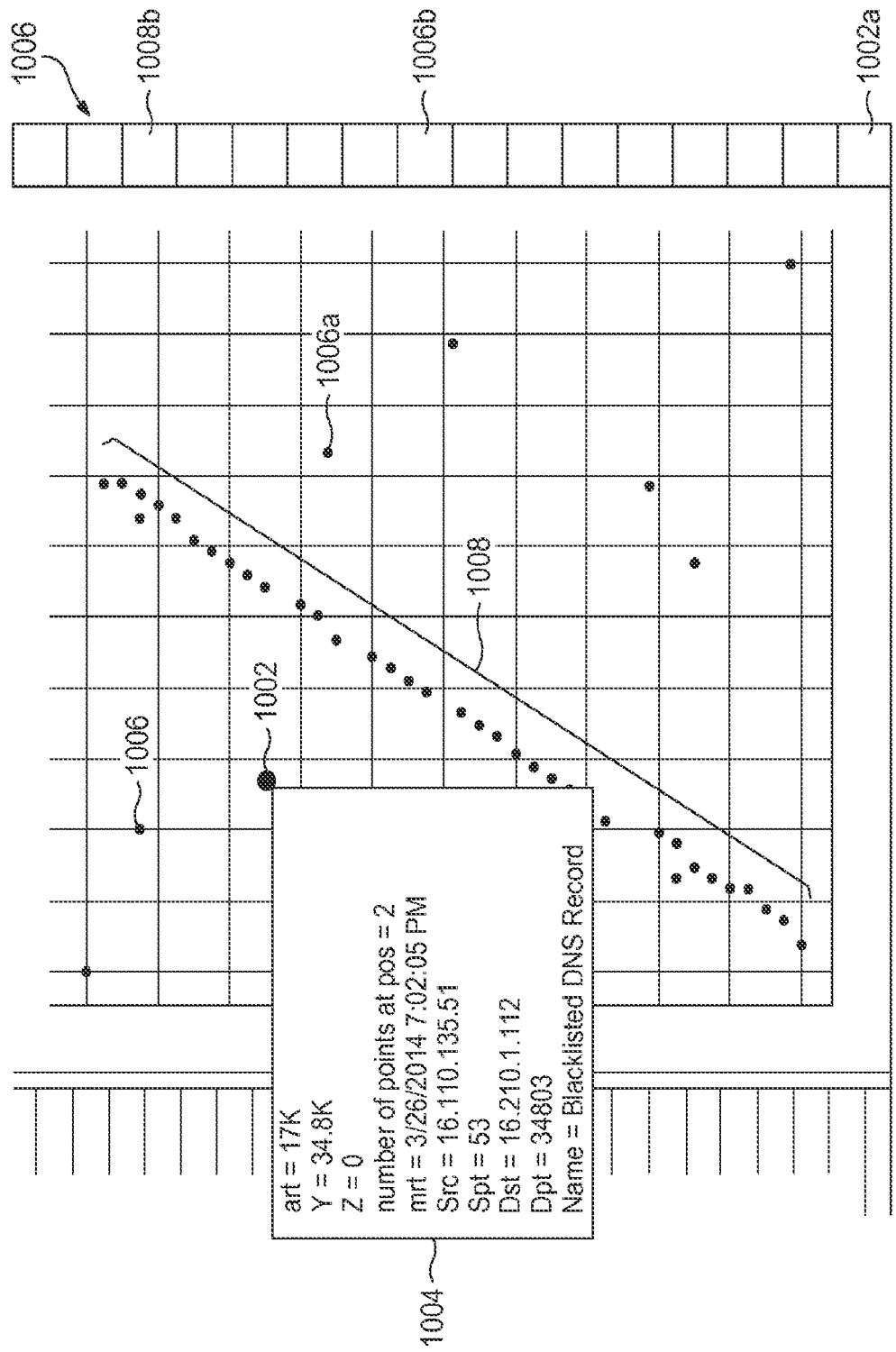
FIG. 10B illustrates another example of highlighting a visual representation of data elements of interest.

FIG. 10B illustrates a blow-up of an example visual representation of FIG. 10A. Some aspects of FIG. 10B may be similar to aspects of system 100 described in FIG. 3B and/or FIG. 6B. In some examples, the similar blacklisted events 1022 and the dissimilar port scan events 1024 may be spatially represented, as for example, diagonal data elements 1008 may represent the dissimilar port scan events 1024 (of FIG. 10A), whereas off-diagonal data elements, such as a first data element 1006, and a second data element 1006*a*, may represent the similar blacklisted events 1022 (of FIG. 10A).

In some examples, the similar blacklisted events 1022 and the dissimilar port scan events 1024 may be visually represented via a color scheme based on the weighted similarity scores. The suspicious attack event represented by the query data element 1002 (of FIG. 10A) is illustrated. In some examples, the query data element 1002 may be associated with a first color 1002*a* (e.g., red) in the color spectrum 1006. Color spectrum 1006 may describe colors based on weighted similarity scores (as described herein). For example, a second color 1006*b* in the color spectrum 1006 may represent the first data element 1006, and the second data element 1006*a* that are in a selected cohort of similar blacklisted events 1022 (as illustrated in FIG. 10A) that are similar to the query data element 1002. In some examples, a spatial representation of the respective cohorts may be based on the weighted similarity scores. For example, the first data element 1006 may be positioned closer to the query data element 1002 than the second data element 1006*a*, because the weighted similarity score for the first data element 1006 is less than the weighted similarity score for the second data element 1006*a*, indicative of a smaller distance between the first data element 1006 and the query data element 1002, than the distance between the second data element 1006*a* and the query data element 1002.

In some examples, a third color 1008*b* in the color spectrum 1006 may represent the diagonal data elements 1008 along a diagonal that are less similar to the query data element 1002. The diagonal data elements 1008 may correspond to the dissimilar port scan events 1024 (as illustrated in FIG. 10A) that are not similar to the query data element 1002. For example, the query data element may correspond to an event "Blacklisted DNS Record", whereas the diagonal data elements 1008 may correspond to an event "Teardown TCP connection." However, as described earlier, the diagonal data elements 1008 may be similar to each other, and may each correspond to the event "Teardown TCP connection."

The pop-up window 1004 (in FIGS. 10A and 10B) may display the plurality of categorical components for the query data element 1002, for example, art=17K, Y=34.8K, Z=0, Number of points at pos=2, Mrt=3/26/2014 7:02:05 PM, src=16.110.135,51", spt=53, dst=16.110.135.51, dpt=34803, Name=Blacklisted DNS Record, and so forth. Such plurality of categorical components may be data from the first row of the excel file format 1008 (of FIG. 10A) representative of the selected blacklisted event 1018.

Referring again to FIG. 1, the components of system 100 may be computing resources, each including a suitable combination of a physical computing device, a virtual computing device, a network, software, a cloud infrastructure, a hybrid cloud infrastructure that includes a first cloud infrastructure and a second cloud infrastructure that is different from the first cloud infrastructure, and so forth. The components of system 100 may be a combination of hardware and programming for performing a designated function. In some instances, each component may include a processor and a memory, while programming code is stored on that memory and executable by a processor to perform a designated function.

For example, display module 104 may comprise a plurality of databases communicatively linked over a network. Display module 104 may include hardware to physically store high-dimensional categorical datasets, and processors to physically process the data. Display module 104 may also include software algorithms to process the datasets and share them over a network. Display module 104 may also include software algorithms to identify real-time selection of a query data element in an interactive visual representation of high-dimensional categorical data elements comprising a plurality of categorical components. Display module 104 may also include software algorithms to provide a cohort of categorical data elements via an interactive graphical user interface. Display module 104 may also include software algorithms to interactively and iteratively validate the cohort of categorical data elements, the validation including receiving, from a user via the interactive graphical user interface, an indication to modify the cohort based on the weighted similarity scores.

Display module 104 may include hardware, such as an interactive graphical user interface, to display a visual representation of the high-dimensional categorical datasets. Also, for example, the display module 104 may include a computing device to provide the graphical user interface. The display module 104 may include software programming to interact with a user select a query data element. The display module 104 may include software programming to interact with a user, such as a domain expert, and receive feedback related to domain knowledge. The display module 104 may also include hardware, including physical processors and memory to house and process such software algorithms, and physical networks to be communicatively linked to the matrix generator 106, evaluator 108, selector 110, and/or the computing devices.

The computing device may be, for example, a web-based server, a local area network server, a cloud-based server, a notebook computer, a desktop computer, an all-in-one system, a tablet computing device, a mobile phone, an electronic book reader, or any other electronic device suitable for provisioning a computing resource to perform a visually interactive identification of a cohort of data objects similar to a query object based on domain knowledge. Computing device may include a processor and a computer-readable storage medium.

As another example, matrix generator 106 may include hardware to physically store the binary distance matrix and/or the category weighting matrix. Matrix generator 106 may also include software algorithms to generate the binary distance matrix and/or the category weighting matrix. Matrix generator 106 may also include software programming to dynamically interact with the display module 104 to receive feedback related to category weights, and update the category weighting matrix accordingly. Matrix generator 106 may also include hardware, including physical processors and memory to house and process such software algorithms, and physical networks to be communicatively linked to the display module 104 and the evaluator 108.

Also, for example, evaluator 108 may include software programming that receives the category weighting matrix from the matrix generator 106. Evaluator 108 may also include software programming to evaluate the weighted similarity scores. Evaluator 108 may also include software programming to dynamically interact with the matrix generator 106 and the selector 110 to receive feedback related to selection of the cohort and/or category weights, and update the weighted similarity scores accordingly. Evaluator 108 may also include hardware, including physical processors and memory to house and process such software algorithms, and physical networks to be communicatively linked to the matrix generator 106 and the selector 110.

As another example, selector 110 may include software programming that receives the weighted similarity scores and the high-dimensional datasets from the evaluator 108. Selector 110 may also include software programming to automatically select a cohort of similar and/or dissimilar categorical data elements based on the respective weighted similarity scores. Selector 110 may also include software programming to rank the high-dimensional datasets based on the weighted similarity scores. Selector 110 may also include software programming to dynamically interact with the display module 104 to receive feedback related to domain knowledge, and refine its selection of the cohort. Selector 110 may include hardware, including physical processors and memory to house and process such software algorithms. Selector 110 may also include physical networks to be communicatively linked to the display module 104, and the evaluator 108.

Figure 11:
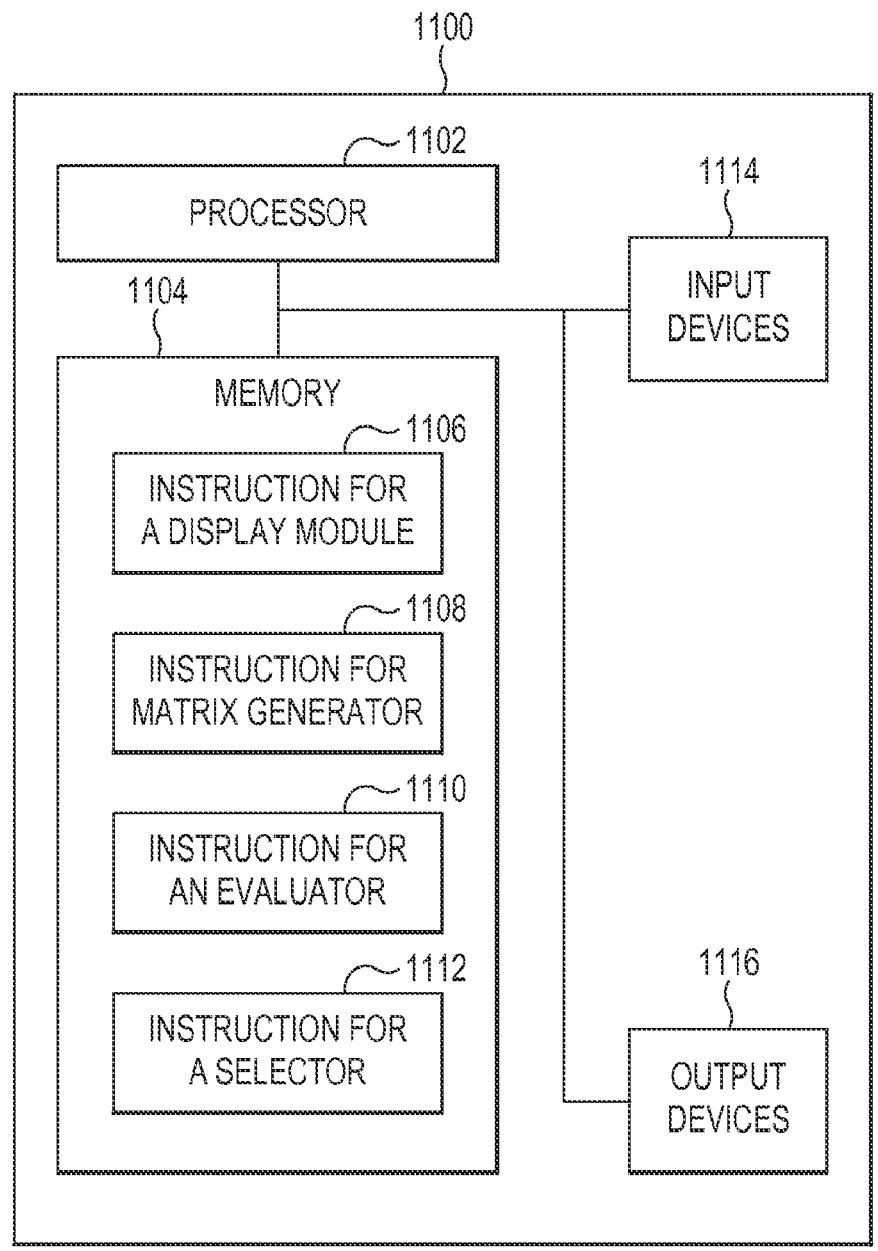
FIG. 11 is a block diagram illustrating one example of a processing system for implementing the system for iterative visualization of a cohort for weighted high-dimensional categorical data.

FIG. 11 is a block diagram illustrating one example of a processing system 1100 for implementing the system 100 for iterative visualization of a cohort for weighted high-dimensional categorical data. Processing system 1100 includes a processor 1102, a memory 1104, input devices 1114, and output devices 1116. High-dimensional categorical data elements may be accessed from an external database (not shown in the figure) that may be interactively linked to the processing system 1100 via the processor 1102. In some examples, the high-dimensional categorical data elements may be stored in the memory 1104 Processor 1102, memory 1104, input devices 1114, and output devices 1116 are coupled to each other through communication link (e.g., a bus).

Processor 1102 includes a Central Processing Unit (CPU) or another suitable processor. In some examples, memory 1104 stores machine readable instructions executed by processor 1102 for operating processing system 1100. Memory 1104 includes any suitable combination of volatile and/or non-volatile memory, such as combinations of Random Access Memory (RAM), Read-Only Memory (ROM), flash memory, and/or other suitable memory.

Memory 1104 stores instructions to be executed by processor 1102 including instructions for a display module 1106, instructions for a matrix generator 1108, instructions for an evaluator 1110, and instructions for a selector 1112. In some examples, the instructions for display module 1106, instructions for matrix generator 1108, instructions for evaluator 1110, and instructions for selector 1112, include the instructions for the display module 104, instructions for the matrix generator 106, instructions for the evaluator 108, and instructions for the selector 110, respectively, as previously described and illustrated with reference to FIG. 1.

Processor 1102 executes instructions for display module 106 to identify real-time selection of a query data element in an interactive visual representation of high-dimensional categorical data elements comprising a plurality of categorical components. In some examples, processor 1102 also executes instructions for display module 1106 to provide a cohort of categorical data elements similar to the query data element, via an interactive graphical user interface. In some examples, processor 1102 also executes instructions for display module 1106 to interactively and iteratively validate the cohort of categorical data elements, the validation including receiving, from a user, an indication to modify the cohort based on updated weighted similarity scores. In some examples, processor 1102 also executes instructions for display module 1106 to represent each data element by a pixel, and where pixel attributes of the pixel represent characteristics of the given data element.

Processor 1102 executes instructions for a matrix generator 1108 to generate a binary distance matrix with columns representing the plurality of categorical components, and entries in, a row indicative of a degree of similarity of respective categorical components of the selected query data element to a data element represented by the row. In some examples, processor 1102 executes instructions for a matrix generator 1108 to determine a category weighting matrix by associating a weight with entries in each column of the binary distance matrix. In some examples, processor 1102 executes instructions for a matrix generator 1108 to determine the category weighting matrix via an iterative and interactive process based on weights received from a user, the weights associated with a relevance of the categorical component represented by the column.

Processor 1102 executes instructions for an evaluator 1110 to evaluate a weighted similarity score for a data element represented by a row of the category weighting matrix based on entries of the row. In some examples, processor 1102 executes instructions for, an evaluator 1110 to evaluate the weighted similarity score for the given data element as a sum of entries of the row, in the category weighting matrix, that represents the given data element, divided by the number of categorical components.

Processor 1102 executes instructions for a selector 1112 to iteratively and interactively select, based on weighted similarity scores, a cohort of categorical data elements for the query data element. In some examples, processor 1102 executes instructions for a selector 1112 to select the cohort of categorical data elements to, comprise data elements not similar to the query data element.

Input devices 1114 include a keyboard, mouse, data ports, and/or other suitable devices for inputting information into processing system 1100. In some examples, input devices 1114, such as a computing device, are used by the interaction processor 1108 to interact with a user. Output devices 1116 include a monitor, speakers, data ports, and/or other suitable devices for outputting information from processing system 1100. In some examples, output devices 1116 are used to provide an interactive visual representation of a selected cohort.

Figure 12:
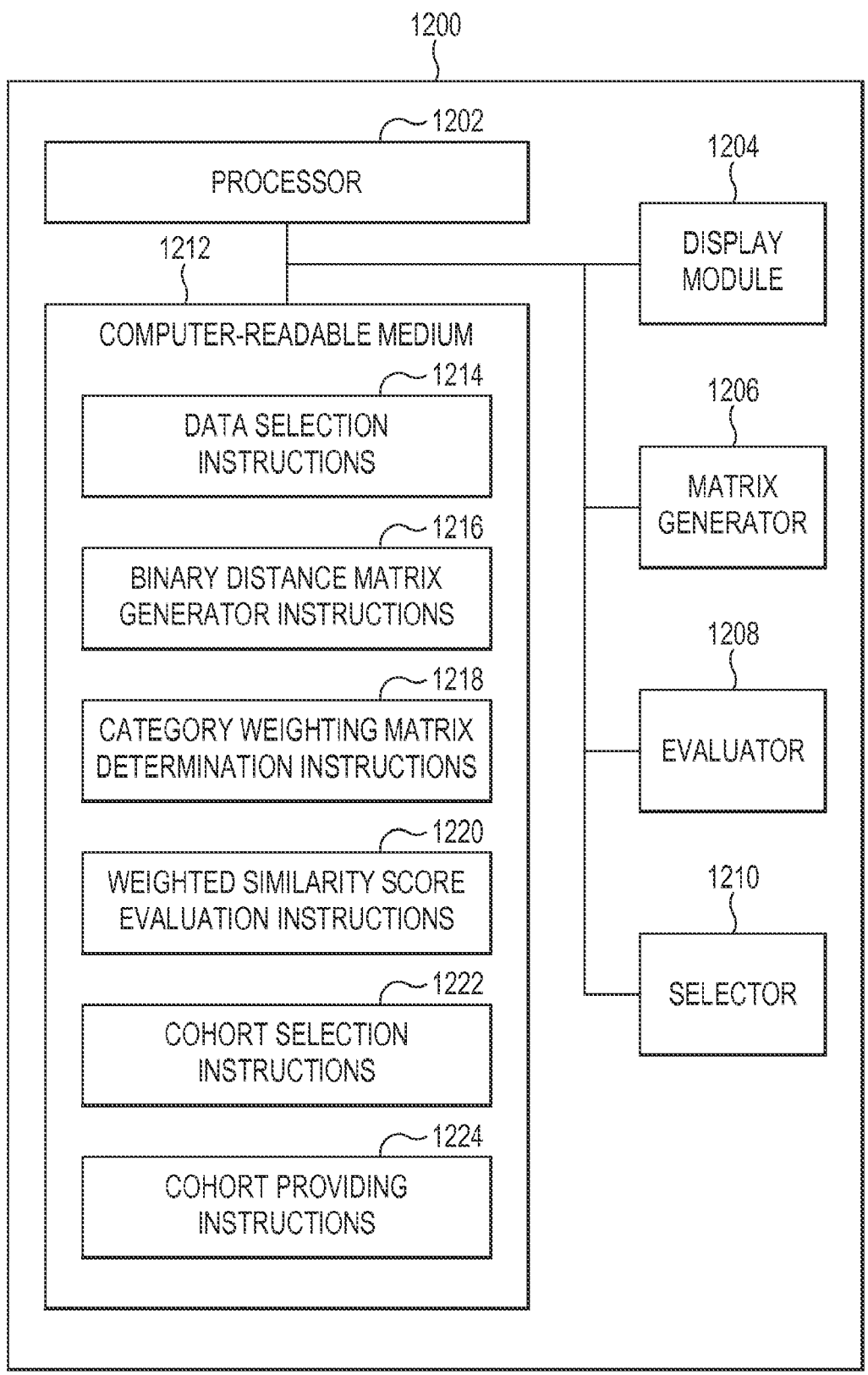
FIG. 12 is a block diagram illustrating one example of a computer readable medium for iterative visualization of a cohort for weighted high-dimensional categorical data.

FIG. 12 is a block diagram illustrating one example of a computer readable medium for iterative visualization of a cohort for weighted high-dimensional categorical data elements. Processing system 1200 includes a processor 1202, a computer readable medium 1212, a display module 1204, a matrix generator 1206, an evaluator 1208, and a selector 1210. Processor 1202, computer readable medium 1212, display module 1204, matrix generator 1206, evaluator 1208, and selector 1210 are coupled to each other through communication link (e.g., a bus). In some examples, display module 1204, matrix generator 1206, evaluator 1208, and selector 1210, include the display module 104, matrix generator 106, evaluator 108, and selector 110, respectively, as previously described and illustrated with reference to FIG. 1.

Processor 1202 executes instructions included in the computer readable medium 1212. Computer readable medium 1212 includes data selection instructions 1214 of a display module 1204 to identify real-time selection, via an interactive graphical user interface, of a query data element in an interactive visual representation of high-dimensional categorical data elements comprising a plurality of categorical component.

Computer readable medium 1212 includes binary distance matrix generation instructions 1216 of a matrix generator 1206 to generate a binary distance matrix with columns representing the plurality of categorical components, and entries in a row indicative of a degree of similarity of respective categorical components of the selected query data element to a data element represented by the row.

Computer readable medium 1212 includes category weighting matrix determination instructions 1218 of a matrix generator 1206 to determine a category weighting matrix by associating a weight with entries in each column of the binary distance matrix.

Computer readable medium 1212 includes weighted similarity score evaluation instructions 1220 of an evaluator 1208 to evaluate a weighted similarity score for a data element represented by a row of the category weighting matrix based on entries of the row.

Computer readable medium 1212 includes cohort selection instructions 1222 of a selector 1210 to iteratively and interactively select, based on weighted similarity scores, a cohort of categorical data elements for the query data element.

Computer readable medium 1212 includes cohort providing instructions 1224 of a display module 1204 to provide the cohort of categorical data elements via the interactive graphical user interface.

As used herein, a "computer readable medium" may be any electronic, magnetic, optical, or other physical storage apparatus to contain or store information such as executable instructions, data, and the like. For example, any computer readable storage medium described herein may be any of Random Access Memory (RAM), volatile memory, non-volatile memory, flash memory, a storage drive (e.g., a hard drive), a solid state drive, and the like, or a combination thereof. For example, the computer readable medium 1212 can include one of or multiple different forms of memory including semiconductor memory devices such as dynamic or static random access memories (DRAMs or SRAMs), erasable and programmable read-only memories (EPROMs), electrically erasable and programmable read-only memories (EEPROMs) and flash memories: magnetic disks such as fixed, floppy and removable disks; other magnetic media including tape; optical media such as compact disks (CDs) or digital video disks (DVDs): or other types of storage devices.

As described herein, various components of the processing system 1200 are identified and refer to a combination of hardware and programming configured to perform a designated function. As illustrated in FIG. 12, the programming may be processor executable instructions stored on tangible computer readable medium 1212, and the hardware may include processor 1202 for executing those instructions. Thus, computer readable medium 1212 may store program instructions that, when executed by processor 1202, implement the various components of the processing system 1200.

Such computer readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

Computer readable medium 1212 may be any of a number of memory components capable of storing instructions that can be executed by processor 1202. Computer readable medium 1212 may be non-transitory in the sense that it does not encompass a transitory signal but instead is made up of one or more memory components configured to store the relevant instructions. Computer readable medium 1212 may be implemented in a single device or distributed across devices. Likewise, processor 1202 represents any number of processors capable of executing instructions stored by computer readable medium 1212, Processor 1202 may be integrated in a single device or distributed across devices. Further, computer readable medium 1212 may be fully or partially integrated in the same device as processor 1202 (as illustrated), or it may be separate but accessible to that device and processor 1202 in some examples, computer readable medium 1212 may be a machine-readable storage medium.

Figure 13:
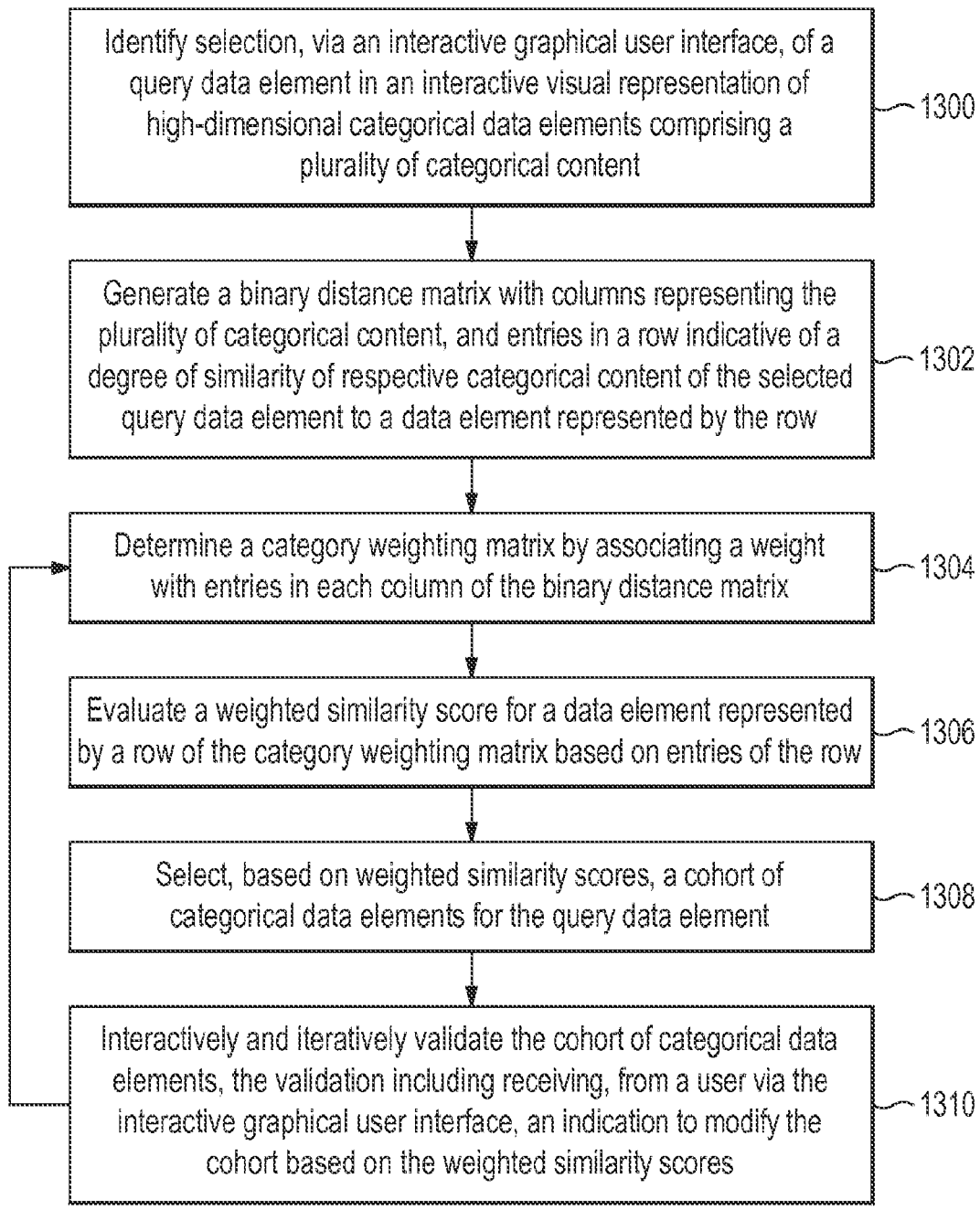
FIG. 13 is a flow diagram illustrating one example of a method for iterative visualization of a cohort for weighted high-dimensional categorical data.

FIG. 13 is a flow diagram illustrating one example of a method for iterative visualization of a cohort for weighted high-dimensional categorical data. At 1300, selection of a query data element in an interactive visual representation of high-dimensional categorical data elements comprising a plurality of categorical components may be identified via an interactive graphical user interface. At 1302, a binary distance matrix may be generated with columns representing the plurality of categorical components, and entries in a row indicative of a degree of similarity of respective categorical components of the selected query data element to a data element represented by the row. At 1304, a category weighting matrix may be determined by associating a weight with entries in each column of the binary distance matrix. At 1306, a weighted similarity score may be evaluated for the data element represented by a row of the category weighting matrix based on entries of the row. At 1308, based on weighted similarity scores, a cohort of categorical data elements may be selected for the query data element. At 1310, the cohort of categorical data elements may be interactively and iteratively validated, the validation including receiving, from a user via the interactive graphical user interface, an indication to modify the cohort based on the weighted similarity scores.

In some examples, the method returns from 1310 to 1304 to perform the interactive and iterative validation. For example, the cohort of categorical data elements may be provided via the interactive graphical user interface, along with a user interactive dissimilarity map for result validation. In some examples, the user may navigate the interactive dissimilarity map to learn the similarity/dissimilarity among different dimensions and to validate the cohort results.

In some examples, the indication to modify may include one of an indication to add a data element to the cohort and an indication to remove a data element from the cohort. For example, the user may indicate that a data element included in the cohort may be removed. Likewise, the user may indicate that a data element not included in the cohort may be included.

In some examples, such inclusion and/or removal of a data element may be a consequence of weights associated with the categorical components. In some examples, the method may include iteratively and interactively receiving the weights from the user via the interactive graphical user interface, where the weights are associated with a relevance of the categorical component represented by the column, and determining the category weighting matrix based on the received weights. For example, at 1310, the user may review the selected cohort and may iteratively vary the weights associated with data elements in the displayed cohort and/or data elements not in the displayed cohort, and provide such weights. An updated category weighting matrix may be determined at 1304. Updated weighted similarity scores may be evaluated at 1306, and an updated cohort may be selected at 1308 based on the updated weighted similarity scores. The updated cohort may be provided to the user, and as described herein, the cohort may be iteratively and interactively modified by the user at 1310.

In some examples, an iterative and interactive cohort selection may be performed to identify data patterns of interest to a user, such as a domain expert.

In some examples, the high-dimensional categorical data elements may be related to one of security data, healthcare data, market consumer data, and product data.

In some examples, the cohort of categorical data elements may comprise data elements not similar to the query data element.

In some examples, each data element of the plurality of data elements may be represented by a pixel in the visual representation.

Examples of the disclosure provide a generalized system for iterative visualization of a cohort for weighted high-dimensional categorical data elements. The generalized system provides a combination of automated visual analytics methods with human interactions to dynamically explore cohorts in big data. Domain experts may be able to refine their hypotheses through interaction and re-process and validate cohorts of categorical data elements based on the visual analytics techniques disclosed herein.

Although specific examples have been illustrated and described herein, especially as related to healthcare data, the examples illustrate applications to any structured data. Accordingly, there may be a variety of alternate and/or equivalent implementations that may be substituted for the specific examples shown and described without departing from the scope of the present disclosure. This application is intended to cover any adaptations or variations of the specific examples discussed herein. Therefore it is intended that this disclosure be limited only by the claims and the equivalents thereof.

The invention claimed is:

1. A visual analytics workflow system comprising:
a display module to identify real-time selection of a query data element in an interactive visual representation of high-dimensional categorical data elements comprising a plurality of categorical components;
a matrix generator to:
generate a binary distance matrix having a plurality of entries organized over a plurality of rows corresponding to the data elements and columns corresponding to the categorical components, each entry indicative of a degree of similarity between the data element corresponding to the row of the entry and the selected data element with respect to the categorical component to which the column of the entry corresponds, and
determine a category weighting matrix having a plurality of entries organized over a plurality of rows corresponding to the data elements and a plurality of rows corresponding to the categorical elements, by, for each column of the binary distance matrix, associating a weight for the categorical element to which the column corresponds with the entries in the column;
an evaluator to evaluate, for each data element other than the selected data element, a weighted similarity score of the data element to the selected data element, based on entries of the row within the category weighting matrix to which the data element corresponds; and
a selector to iteratively and interactively select, based on the weighted similarity scores for the data elements other than the selected data element, a cohort of the other data elements for the selected data element categorical data elements for the query data element.

2. The system of claim 1, wherein the matrix generator determines the category weighting matrix via an iterative and interactive process based on weights received from a user, the weights associated with a relevance of the categorical component represented by the column.

3. The system of claim 1, wherein the display module further provides the cohort of categorical data elements via an interactive graphical user interface.

4. The system of claim 3, further comprising interactive and iterative validation of the cohort of categorical data elements, the validation including receiving, from a user, an indication to modify the cohort based on the weighted similarity scores.

5. The system of claim 4, wherein the indication to modify includes one of an indication to add a data element to the cohort and an indication to remove a data element from the cohort.

6. The system of claim 1, wherein a matrix entry 0 represents identical categorical components, and 1 represents non-identical categorical components.

7. The system of claim 6, wherein the matrix entry 1 is substituted with a value between 0 and 1, the value indicative of a degree of difference of the non-identical content.

8. The system of claim 1, wherein the cohort of categorical data elements comprises data elements not similar to the query data element.

9. The system of claim 1, wherein each data element is represented by a pixel, and wherein pixel attributes of the pixel represent characteristics of the given data element.

10. The system of claim 1, wherein the categorical components includes an IP address, a port number, a geolocation, and a protocol.

11. The system of claim 1, wherein the weighted similarity score for the given data element is a sum of entries of the row, in the category weighting matrix, that represents the given data element, divided by the number of categorical components.

12. A visual analytics workflow method comprising:
identifying selection, via an interactive graphical user interface, of a query data element in an interactive visual representation of high-dimensional categorical data elements comprising a plurality of categorical components;
generating a binary distance matrix having a plurality of entries organized over a plurality of rows corresponding to the data elements and columns corresponding to the categorical components, each entry indicative of a degree of similarity between the data element corresponding to the row of the entry and the selected data element with respect to the categorical component to which the column of the entry corresponds;
determining a category weighting matrix having a plurality of entries organized over a plurality of rows corresponding to the data elements and a plurality of rows corresponding to the categorical elements, by, for each column of the binary distance matrix, associating a weight for the categorical element to which the column corresponds with the entries in the column;
evaluating, for each data element other than the selected data element, a weighted similarity score of the data element to the selected data element, based on entries of the row within the category weighting matrix to which the data element corresponds;
selecting, based on the weighted similarity scores for the data elements other than the selected data element, a cohort of the other data elements for the selected data element categorical data elements for the data element; and
interactively and iteratively validating the cohort, the validation including receiving, from a user via the interactive graphical user interface, an indication to modify the cohort.

13. The method of claim 12, further comprising:
iteratively and interactively receiving the weights from the user via the interactive graphical user interface, the weights associated with a relevance of the categorical component represented by the column; and
determining the category weighting matrix based on the received weights.

14. The method of claim 12, wherein the high-dimensional categorical data elements are related to one of security data, healthcare data, market consumer data, and product data.

15. A non-transitory computer readable medium comprising executable instructions to:
identify selection, via an interactive graphical user interface, of a query data element in an interactive visual representation of high-dimensional categorical data elements comprising a plurality of categorical components;
generate a binary distance matrix having a plurality of entries organized over a plurality of rows corresponding to the data elements and columns corresponding to the categorical components, each entry indicative of a degree of similarity between the data element corresponding to the row of the entry and the selected data element with respect to the categorical component to which the column of the entry corresponds;

determine a category weighting matrix having a plurality of entries organized over a plurality of rows corresponding to the data elements and a plurality of rows corresponding to the categorical elements, by, for each column of the binary distance matrix, associating a weight for the categorical element to which the column corresponds with the entries in the column;

evaluate, for each data element other than the selected data element, a weighted similarity score of the data element to the selected data element, based on entries of the row within the category weighting matrix to which the data element corresponds;

select, based on the weighted similarity scores for the data elements other than the selected data element, a cohort of the other data elements for the selected data element categorical data elements for the data element; and provide the cohort via the interactive graphical user interface.

* * * * *